United States Patent [19]

Matkin et al.

[11] Patent Number: 5,646,324
[45] Date of Patent: Jul. 8, 1997

[54] ZINC GLYCEROLATE MANUFACTURE

[75] Inventors: David A. Matkin, Maidenhead; Dennis C. Renshaw, Manchester; Anthony R. Harrison, Shevington, all of United Kingdom

[73] Assignees: Pharmaserve Limited, Manchester; Stiefel Laboratories (Ireland) Limited, Berkshire, both of United Kingdom

[21] Appl. No.: 612,837

[22] PCT Filed: Sep. 22, 1994

[86] PCT No.: PCT/GB94/02059

§ 371 Date: May 14, 1996

§ 102(e) Date: May 14, 1996

[87] PCT Pub. No.: WO95/08524

PCT Pub. Date: Mar. 30, 1995

[30] Foreign Application Priority Data

Sep. 23, 1993 [GB] United Kingdom ............... 9319675
Apr. 12, 1994 [GB] United Kingdom ............... 9407230

[51] Int. Cl.⁶ .................................................. C07F 3/06
[52] U.S. Cl. ............................................................ 556/130
[58] Field of Search .............................................. 556/130

[56] References Cited

U.S. PATENT DOCUMENTS 4,544,761  10/1985  Taylor et al. .......................... 556/130
5,475,123  12/1995  Bos ....................................... 556/130

FOREIGN PATENT DOCUMENTS

WO8701281  3/1987  WIPO.
WO8701379  4/1987  WIPO.
WO8805035  7/1988  WIPO.
WO9302130  2/1993  WIPO.

OTHER PUBLICATIONS

Apisariyakulm, A., et al., The Medical Journal of Australia, 152, p. 54, Jan. 1990.

*Primary Examiner*—Porfirio Nazario-Gonzalez

[57] ABSTRACT

Zinc glycerolate comprised of plate-like crystals is prepared by heating a mixture of zinc oxide, or zinc oxide precursor compound, with glycerol at 15° C. to 105° C., usually at least 45° C. Excess glycerol can be removed from the crude zinc glycerolate product by washing at least once with a $C_1$–$C_4$ alkanol, preferably isopropanol.

11 Claims, No Drawings

ZINC GLYCEROLATE MANUFACTURE

This application was filed under 35 U.S.C. §371 as a request for U.S. examination of International application No. PCT/GB94/02059, filed Sep. 22, 1994.

The present invention relates to zinc glycerolate and provides an improved process for the preparation thereof.

"Zinc glycerolate" as used herein means a slippery tactile insoluble material comprised of plate-like crystals having relatively low thickness and high lubricity formed by heating zinc oxide (or a zinc oxide precursor compound) with glycerol. As used herein, the term "zinc oxide precursor compound" means a zinc compound which will decompose to or form zinc oxide under the reaction conditions. Typically the crystals are of 1 to 100, usually 10 to 100, micrometer particle size. Zinc glycerolate is known under the Trade Mark GLYZINC and has cosmetic and pharmaceutical as well as industrial uses.

Radoslovich et al (Austral. J. Chem. 23 (1970) 1963–1970) first disclosed that crystalline metal complexes were formed by heating certain metal oxides, hydroxides or salts with glycerol at temperatures above 110° C. The metals are cobalt, iron, manganese and zinc and the complexes formed differ from those previously obtained by reaction in aqueous solution at room temperature in that they are insoluble in water and organic solvents. The zinc comp ("glycerolatozinc (II)") reportedly was obtained from zinc carbonate at 160° C., from zinc acetate at 110°C. to 160°C., and from zinc hydroxide at 200°C. but no experimental data is provided. It is reported that slow heating produced well developed crystals at 110° C. but that higher temperatures were required to obtain smaller plates. The particle size and tactility of these products is not reported but, as reported below, subsequently it has been assumed that temperatures of at least 120°C. were required to obtain zinc glycerolate (as that term is used herein).

Fairlie et al (Agents and Actions 36 (1992) 152–158) refers to the use of zinc to treat local skin disorders and some forms of systemic inflammatory disease, including arthritis. Reference is made in the opening paragraph of the Introduction to forming Glyzinc by heating zinc oxide with glycerol at 200° to 300° C. In the exemplified process, a dispersion of zinc hydroxide in ethanol is heated with glycerol to 120° C. until ethanol and absorbed water evaporates and then the temperature is raised to 240°–275° C. for one hour to expel water.

WO-A-8201867 (published 10th Jun. 1982) discloses the use of zinc glycerolate for cosmetic, prophylactic and therapeutic purposes. Specific reference is made to its use in treating ammoniacal dermatitis in babies (nappy rash) and pruritus; for alleviating psoriasis; for preventing fungal or bacterial decomposition of tissue and the resulting odours, especially in tinea pedis; for preventing industrial dermatitis; and for treating ichthyosis. The zinc glycerolate is specified to be of 10 to 100 micrometer particle size and to be the reaction product of zinc oxide (or a zinc oxide precursor compound) with glycerol at 120° C. to 300° C. It is stated that the reaction of zinc oxide with glycerol proceeds slowly below 200° C. but very rapidly above 220° C. The only specified reactant ratio of zinc compound to glycerol is 1:10.

The preferred methods of preparing zinc glycerolate specified in WO-A-8201867 are (a) heating a mixture of zinc oxide (or zinc oxide precursor compound) with glycerol at a temperature of about 260° C.; (b) adding zinc oxide (or zinc oxide precursor compound) to glycerol at 120° C.; and then increasing the temperature of the mixture to about 260° C.; and (c) adding zinc oxide (or zinc oxide precursor compound) to glycerol at 220° C. and then increasing the temperature of the mixture to about 260° C. Process (a) is exemplified in Example 4 using zinc oxide; process (b) is exemplfied in Example 2 using zinc oxide; process (c) is exemplified in Examples 1 and 3 using zinc oxide and zinc acetate respectively. In all four Examples, the mixture was heated at 260° C. for 1 hour. Crude zinc glycerolate is separated from the reaction mixture by filtering and then washing first with ethanol and then with acetone before being dried.

WO-A-8701281 (published 12th Mar. 1987) discloses the percutaneous, subcutaneous and intramuscular as well as oral administration of zinc glycerolate. It specifically refers to the use of zinc glycerolate in the treatment of diabetes; as an antimicrobial or antibacterial agent; for the treatment of zinc deficiency; as an anti-inflammatory agent, especially in the treatment of arthritis and psoriasis; and as a gastroprotective agent, especially in the treatment of gastric ulcers. As in WO-A-8201867,it is specified that the zinc glycerolate is the reaction product of the zinc oxide (or a zinc oxide precursor compound) with glycerol at 120° to 300° C. There is no exemplification of the manufacture of zinc glycerolate.

WO-A-8701379 (also published 12th Mar. 1987) discloses the use of zinc glycerolate as a UV-shielding material and bonding agent in rubbers and plastics. It is specified that the zinc glycerolate is prepared by mixing zinc oxide (or a zinc oxide precursor compound) with glycerol at a temperature of about 260° C. and, after cooling, pouring the mixture into water, filtering, washing and drying. It is stated that the reaction will proceed at lower (unspecified) temperatures more slowly. The only specified reactant ratio of zinc compound to glycerol is 1:10. There is no exemplification of the manufacture of zinc glycerolate.

WO-A-8805035 (published 14th Jul. 1988) discloses the prepartion od zinc glycerolate by exposing a solution or suspension cf a zinc compound in glycerol to microwave radiation. An object of the invention is to avoid the high temperatures required in the convention process. The exemplified zinc compounds are zinc acetate and zinc hydroxide but there is no exemplification of the manufacture of zinc glycerolate.

Apisariyakulm et al (The Medical Journal of Australia 152 (1990) 54) discloses the use of zinc glycerolate in the treatment of oral herpetic sores.

WO-A-9302130 (published 4th Feb. 1993) discloses a flexible gas-permeable polymeric film incorporating zinc glycerolate for use in the modified atmosphere packaging of fresh produce, especially flowers, fruit and vegetables, to extend the post harvest life thereof. No reference is made to the process by which the zinc glycerolate is prepared.

The present methods of preparing zinc glycerolate are not entirely satisfactory. The use of temperatures in excess of 120° C. or of microwave irradiation requires special and relatively expensive equipment. In particular, conventional steam-heated mixers cannot be used. Further, crude zinc glycerolate is not readily separated from the reaction medium using conventional filtering equipment and excess glycerol is not readily removed from the filtrate using ethanol and/or acetone washes.

It has surprisingly been found that, contrary to the teaching of the prior art, zinc glycerolate can readily be prepared from zinc oxide (or a zinc oxide precursor compound) at temperatures below 110° C. and that the zinc glycerolate thus obtained is not inferior to that prepared by the known processes and can be of pharmaceutically acceptable quality. Further its has been found that the crude zinc glycerolate can readily be separated from the reaction mixture by centrifuging and also that glycerol is readily and completely removed from the residue by simultaneously or alternately washing with $C_1$–$C_4$ alkanol, especially isopropanol, and centrifuging.

According to the present invention, there is a provided a process for preparing zinc glycerolate by heating a mixture of zinc oxide, or a zinc oxide precursor compound, with glycerol, characterized in that the reaction temperature is 15° C. to 105° C.

It is preferred to use zinc oxide but any zinc compound, such as zinc hydroxide, zinc acetate or zinc carbonate, which forms zinc oxide under the reaction conditions can be used.

Preferably, the reaction is conducted in the presence of a weak Lewis acid or base, in the form of the free acid or base or as a salt thereof, as catalyst. The catalyst will be chosen having regard to the ease of removal from the zinc glycerolate product. Presently, it is preferred that the catalyst is an aliphatic or aromatic carboxylic acid or salt, especially zinc salt, or a metal carbonate, especially an alkali metal or zinc carbonate. Especially preferred catalysts are $C_2$–$C_6$ primary carboxylic acids or zinc salts thereof, for example citric acid or zinc citrate or, particularly, acetic acid or zinc acetate. Other suitable catalysts include sodium carbonate and salicylic acid. Usually, the catalyst is present in an amount up to 15%, preferably 5 to 10%, by weight of the zinc oxide or zinc oxide precursor compound (unless said compound is itself a catalyst).

Usually the glycerol will be present in a 3 to 10 fold excess by weight over the zinc oxide or zinc oxide precursor compound. Unlike the prior art process using higher temperatures (where a 10 fold increase is preferred), it is preferred that the weight ratio of zinc oxide, or zinc oxide precursor compound, to glycerol is in the range 1:4 to 1.8, especially 1:5 to 1:8, particularly about 1:6. Lower ratios down to 1:1 may be used by using heavy duty mixing equipment or by conducting the reaction in an inert solvent to compensate for the high viscosity which otherwise accompanies the use of ratios below 1:4.

The use of a reaction temperature below 110° C. enables the process to be carried out in conventional steam-heated mixing equipment. Although the reaction can proceed at room temperature, the reaction mixture usually will be heated to at least 45° C. Suitably, the temperature is in the range 55° C. to 105° C., preferably 80° C. to 105° C., especially about 100° C. It is particularly surprising that the reaction proceeds at temperatures below 100° C. since formation of the zinc glycerolate is a condensation reaction and it was to be expected that the temperature should be high enough to drive off water formed as by-product.

Usually the reaction mixture will be heated for 0.5 to 10 hours, preferably 30 to 120 minutes, especially 60 to 90 minutes, whilst stirring. It may be possible to reduce reaction times and/or to control product particle size by seeding the reaction mixture with, for example, glycerol recycled from a previous reaction batch.

As mentioned previously, it has been found that the crude zinc glycerolate can readily and efficiently be separated from the reaction mixture by centrifuging and convention industrial centrifuges can be used for this purpose. Suitably, the bulk of the excess glycerol is removed by filtration of the hot reaction mixture prior to centrifuging.

The crude zinc glycerolate remaining after centrifuging contains glycerol in excess of the amount acceptable for pharmaceutical use. As already known, this glycerol contamination can be removed by washing the crude zinc glycerolate with a volatile non-aqueous solvent. Suitably, ethanol or other $C_1$–$C_4$ alkanol can be used. However, it has been found that isopropanol is the most effective solvent for removal of glycerol from the crude zinc glycerolate. Further, it is preferred that the residual glycerol is removed by simultaneous or, especially, alternate washing and centrifuging. Usually, 2 to 5, especially 3, washing and centrifuging cycles will be required. Residual solvent can readily be removed from the washed zinc glycerolate by heating.

The zinc glycerolate product of the present invention is chemically and morphologically identical with zinc glycerolate prepared by the prior art process using higher temperatures. Accordingly, it can be used for all the known uses of zinc glycerolate. The use of lower reaction temperatures without the use of microwave irradiation reduces the cost of manufacture compared with the prior art processes. Moreover, the embodiment in which excess glycerol is removed by washing with isopropanol readily provides an essentially glycerol-free product which is particularly suitable for pharmaceutical use.

The process of the invention is exemplified in the following non-limiting Examples.

EXAMPLE 1

Glycerol (150 kg), zinc oxide (25 kg) and zinc acetate (2 kg) were mixed together for about 15 minutes until a uniform slurry was obtained. The slurry was heated to 105° C. and mixing at that temperature was continued for 90 minutes. It was then cooled to 35° C. to 40° C. and mixed for about 15 minutes with isopropanol (75 kg) to form a uniform slurry. This slurry was centrifuged for 30 minutes and the isopropanol washing and centrifuging cycle repeated three times. The final centrifuge residue was spread evenly on trays-and dried at 80° C. for 6 hours to obtain a white powder in good yield. The powder was confirmed to be zinc glycerolate by both elemental analysis and IR spectroscopy. It was substantially free of glycerol and had essentially the same morphology as zinc glycerolate prepared by the analogous prior art method in which the glycerol, zinc oxide and zinc acetate were heated at above 120° C.

EXAMPLE 2

The procedure of Example 1 was essentially repeated except that the slurry was heated at 65° C. for seven hours and the slurry was filtered while still hot. After the centrifuging and isopropanol washing, zinc glycerolate is obtained in good yield and is substantially free of glycerol and has essentially the same morphology as zinc glycerolate prepared by the analogous prior art method.

EXAMPLE 3

The procedure of Example 1 was essentially repeated except that the slurry was heated at 55° C. for seven hours and the slurry was filtered while still hot. After the centrifuging and isopropanol washing, zinc glycerolate is obtained in good yield and is substantially free of glycerol and has essentially the same morphology as zinc glycerolate prepared by the analogous prior art method.

EXAMPLE 4

The procedure of Example 1 was essentially repeated except that the slurry was heated at 45° C. for ten hours and the slurry was filtered while still hot. The product contained in good yield zinc glycerolate having essentially the same morphology as zinc glycerolate prepared by the analogous prior art method.

Comparative Example A

The procedure of Example 1 was essentially repeated using glycerol (100 cm$^3$), copper (1) oxide (16.67 g) and acetic acid (to pH 5). The slurry was heated at 80° C. for 5 hours and centrifuged with 3 washes. The residue was dried at 80° C. to produce a red/brown powder. From analysis using IR spectroscopy it was found that no glycerato complex was obtained.

Comparative Example B

The procedure of Example 1 was essentially repeated using glycerol (66.67 cm$_3$), copper (II) oxide (16.67 g) and acetic acid (to pH 5.2). The slurry was heated at 100° C. for 2½ hours and, when left to cool, became quite viscous especially near bottom of the container. The slurry was centrifuged with 3 washes and dried at 80° C. to produce a black powder. From analysis using IR spectroscopy it was found that no glycerato complex was obtained.

Comparative Examples A and B indicate that copper oxide cannot be substituted for zinc oxide in the process of Example 1.

EXAMPLE 5

The procedure of Example 1 was essentially repeated using glycerol (66.67 cm$^3$) and zinc oxide (16.67 g) but no catalyst (zinc acetate). The slurry was heated at 100° C. for 2½ hours, centrifuged with 3 washes, and dried at 80° C. to produce a white powder in low yield. From analysis using IR spectroscopy it was found that a glycerato complex was obtained having essentially the same morphology as the zinc glycerolate prepared by the analogous prior art method.

EXAMPLE 6

The procedure of Example 1 was essentially repeated using glycerol (100 cm$^3$) and zinc oxide (16.67 g) but with sodium carbonate (1.33 g) as catalyst instead of zinc acetate. The slurry was heated at 100° C. for 2 hours, centrifuged with 3 washes, and dried at 90° C. to produce a white powder in good yield. From analysis using IR spectroscopy it was found that a glycerato complex was obtained having essentially the same morphology as the zinc glycerolate prepared by the analogous prior art method.

EXAMPLE 7

The procedure of Example 1 was essentially repeated using glycerol (100 cm$^3$), zinc oxide (16.67 g) and acetic acid (to pH 5). The slurry was heated at 100° C. for 2½ hours, centrifuged with 3 washes, and dried at 80° C. to produce a white powder in good yield. From analysis using IR spectroscopy it was found that a glycerato complex was obtained having essentially the same morphology as the zinc glycerolate prepared by the analogous prior art method.

EXAMPLE 8

The procedure of Example 1 was essentially repeated using glycerol (66.67 cm$_3$), zinc oxide (16.67 g) but with salicylic acid (1.33 g; to pH 5.9) as catalyst instead of zinc acetate. The slurry was heated at 100° C. for 2 hours but became very thick after 1 hour and quite viscous when left to cool. It was centrifuged with 6 washes to produce a glycerol-free substance, then dried at 80° C. to produce a white powder in reasonable yield. From analysis using IR spectroscopy it was found that a glycerato complex was obtained having essentially the same morphology as the zinc glycerolate prepared by the analogous prior art method.

Comparative Example C

The procedure of Example 1 was essentially repeated using glycerol (66,67 cm$^3$) and zinc oxide (16.67 g) but with phosphoric acid (0.153 g; to pH 3.1), as catalyst instead of zinc acetate. The slurry was heated at 100° C. for 2 hours, centrifuged with 4 washes, and dried at 80° C. to produce a white powder. From analysis using IR spectroscopy it was found that no glycerato complex was obtained.

Comparative Example D

The procedure of Comparative Example C was essentially repeated except that the amount of phosphoric acid (0.087 g) was reduced so that the pH of the mixture was pH 5.2. From analysis using IR spectroscopy it was found that no glycerato complex was obtained.

Comparative Example E

The procedure of Comparative Example C was essentially repeated except that the amount of phosphoric acid (1.563 g) was increased sot that the ph of the mixture was ph 2.0 addition of the acid, the mixture became every hot and turned almost solid while mixing: From analysis using IR spectroscopy it was found that no glycerato complex was obtained.

Comparative Example F

The procedure of Comparative Example C was essentially repeated except that alcoholic KOH (0.366 g; to pH 9.0) was used instead of phosphoric acid. From analysis using IR spectroscopy it was found that no glycerato complex was obtained.

Comparative Examples C to D indicate that a strong acid or strong base cannot be used as a catalyst for process of Example 1.

EXAMPLE 9

The procedure of Comparative Example C was essentially repeated except that no phosphoric acid was used, whereby the mixture had pH 7.0. A glycerato complex was obtained in low yield. IR spectroscopy established that it had essentially the same morphology as the zinc glycerolate prepared by the analogous prior art method.

EXAMPLE 10

The procedure of Example 1 was essentially repeated using glycerol (66.67 cm$^3$) and zinc oxide (16.67 g) but with acetic acid (0.198 g; to pH 5.1) as catalyst instead of zinc acetate. The slurry was heated at 100° C. for 2 hours, centrifuged with 4 washes, and dried at 80° C. to produce a white powder in good yield. From analysis using IR spectroscopy it was found that a glycerato complex was obtained having essentially the morphology as the zinc glycerolate prepared by the analogous prior art method.

EXAMPLE 11

The procedure of Example 10 was essentially repeated except that the amount of acetic acid (0.074 g) was reduced so that the pH of the mixture was pH 5.8. A glycerato complex was obtained in low yield. IR spectroscopy established that it had essentially the same morphology as the zinc glycerolate prepared by the analogous prior art method.

EXAMPLE 12

The procedure of Example 10 was essentially repeated except that the amount of acetic acid (0.855 g) was increased. The pH of the mixture was pH 4.5 even after addition of excess acid. The mixture became very thick after 1 hour and extremely viscous after 2 hours. A glycerato complex was obtained in good yield but several washes were required to separate the glycerol. IR spectroscopy established that it had essentially the same morphology as the zinc glycerolate prepared by the analogous prior art method.

EXAMPLE 13

The procedure of Example 10 was essentially repeated except that the amount of acetic acid (1.013 g) was increased. The pH of the mixture was unknown. As in Example 12, the mixture became very thick after 1 hour and extremely viscous after 2 hours. A glycerato complex was obtained in good yield but several washes were required to separate the glycerol. IR spectroscopy established that it had essentially the same morphology as the zinc glycerolate prepared by the analogous prior art method.

EXAMPLE 14

The procedure of Example 10 was essentially repeated except that the amount of acetic acid 0.09 g) was reduced so that the pH of the mixture was pH 5.25 and the slurry was mixed at room temperature (about 20° C.) A glycerato complex was obtained in low yield. IR spectroscopy established that it had essentially the same morphology as the zinc glycerolate prepared by the analogous prior art method.

EXAMPLE 15

The procedure of Example 10 was essentially repeated except that the amount of acetic acid (0.122 g) was reduced so that the pH of the mixture was pH 5.2 and the slurry was heated at 55° C. A glycerato complex was obtained in reasonable yield. IR spectroscopy established that it had essentially the same morphology as the zinc glycerolate prepared by the analogous prior art method.

EXAMPLE 16

The procedure of Example 1 was essentially repeated using glycerol (16.67 cm$^3$) and zinc oxide (16.67 g) but with acetic acid (0.265 g; to pH 5.2) instead of zinc acetate and in the presence of light liquid paraffin (50.0 cm$^3$). The slurry was heated at 100° C. for 2 hours, centrifuged with 4 washes, and dried at 80° C. to produce a white powder in good yield. From analysis using IR spectroscopy it was found that a glycerato complex was obtained having essentially the same morphology as the zinc glycerolate prepared by the analogous prior art method.

EXAMPLE 17

The procedure of Example 16 was essentially repeated except that isopropanol (50 cm$_3$) was used instead of light liquid paraffin and the amount of acetic acid (0.317 g; to pH 5.3) was increased and the mixture was heated at 55°–60° C. A glycerato complex was obtained in reasonable yield. IR spectroscopy established that it had essentially the same morphology as the zinc glycerolate prepared by the analogous prior art method.

Comparative Example G

The procedure of Example 1 was essentially repeated using glycerol (66.67 cm$_3$) and acetic acid (0.064 g; to pH 4.8) but with zinc stearate (16.67 g) instead of zinc oxide. Zinc stearate does not form zinc oxide under the reaction conditions employed. The slurry was heated at 100° C. for 2 hours, centrifuged with 4 washes, and dried at 80° C. to produce a white powder. From analysis using IR spectroscopy it was found that no glycerato complex was obtained.

Comparative Example H

The procedure of Example 1 was essentially repeated using glycerol (66.67 cm$^3$) but with $ZnCl_2$ (16.67 g) instead of zinc oxide and no zinc acetate. $ZnCl_2$, does not form zinc oxide under the reaction conditions employed. The mixture had pH 2.2 even after addition of alcoholic KOH. The solution was heated at 100° C. for 2 hours but no slurry was produced and no thickening was observed ($ZnCl_2$ dissolves in glycerol); it remained very runny (water like) throughout stirring. The solution was centrifuged and no residue was obtained. The test was abandoned and sanctioned void, so no I.R. spectroscopy was done for identification of glycerato complexes.

Comparative Examples G and H that a zinc salt which does not form zinc oxide under the reaction conditions cannot be used as a zinc source for process of Example 1.

I claim:

1. A process for preparing zinc glycerolate by heating a mixture of zinc oxide, or zinc oxide precursor compound, with glycerol, characterized in that the reaction temperature is 15° C. to 105° C.

2. A process as claimed in claim 1, wherein the reaction temperature is in the range 45°C. to 105° C.

3. A process as claimed in claim 1, wherein the reaction temperature is below 100° C.

4. A process as claimed in claim 1, wherein the reaction mixture comprises zinc oxide and glycerol.

5. A process as claimed in claim 1, wherein the reaction is conducted in the presence of a weak Lewis acid or base, or salt thereof, as catalyst.

6. A process as claimed in claim 5, wherein the catalyst is an aliphatic or aromatic carboxylic acid or salt or a metal carbonate.

7. A process as claimed in claim 6, wherein the catalyst is acetic acid or zinc acetate.

8. A process as claimed in claim 1, wherein the weight ratio of zinc oxide, or zinc oxide precursor compound, to glycerol is in the range 1:1 to 1:10.

9. A process as claimed in claim 8, wherein said ratio is in the range 1:5 to 1:8.

10. A process as claimed in claim 1, wherein crude zinc glycerolate is washed with a $C_1$–$C_4$ alkanol to remove residual glycerol.

11. A process as claimed in claim 10, wherein the alkanol is isopropanol.

* * * * *